United States Patent [19]
Vaghefi

[11] Patent Number: 5,859,234
[45] Date of Patent: Jan. 12, 1999

[54] 2'-O-METHYL CYTIDINE MONOMER USEFUL IN OLIGONUCLEOTIDE SYNTHESIS

[75] Inventor: Morteza M. Vaghefi, San Diego, Calif.

[73] Assignee: Genta, Incorporated, San Diego, Calif.

[21] Appl. No.: 727,139

[22] Filed: Oct. 8, 1996

Related U.S. Application Data

[62] Division of Ser. No. 893,374, Jun. 3, 1992, Pat. No. 5,606,049.

[51] Int. Cl.$^6$ .................................................. C07H 19/067
[52] U.S. Cl. .................... 536/26.8; 536/25.34; 536/28.5; 536/28.51; 536/28.52
[58] Field of Search ................................ 536/26.8, 25.34, 536/28.5, 28.51, 28.52

[56] References Cited

U.S. PATENT DOCUMENTS

| | | | |
|---|---|---|---|
| 5,214,135 | 5/1993 | Srivastava et al. | 536/26.7 |
| 5,525,719 | 6/1996 | Srivastava et al. | 536/26.7 |

FOREIGN PATENT DOCUMENTS

| | | |
|---|---|---|
| 9301204 | 1/1993 | WIPO . |
| 9618638 | 6/1996 | WIPO . |

OTHER PUBLICATIONS

Edmonds, et al., *Structural Characterizationof Four Ribose–methylated Nucleosides from the Transfer RNA of Extremely Thermophilic Archaebacteria*, J. Chem. Soc., Chem. Commun., pp. 909–910, (1987) Month of publication is unavailable.
Greene, et al., *Protection for the Hydroxyl Group, Including 1,2– and 1,3–Diols,* Protective Groups in Organic Synthesis, pp. 68–86, (1991) Month of publication is unavailable.
Heikkila, et al., *A "One–Pot" Synthesis of 4–B–Benzoyl–2'–O–Mehtylcytidine and its Application as a Key Building Block in tRNA Chemistry,* Chemica Scripta., 20:251–252, (1982) Month of publication is unavailable.
Kawai, et al., *Relation between functions and conformational characteristics of modified nucleosides found in tRNAs,* Nucleic Acids Research Symposium Series, 25:49–50, (1991) Month of publication is unavailable.
Kawai, et al., *Conformationa Rigidity of $N^4$–Acetyl–2'–O–Methylcytidine Found In tRNA of Extremely Thermophilic Archaebacteria,* Nucleosides and Nucleotides, 11(2–4):759–771 (1992) Month of publication is unavailable.
Markiewicz, et al., *The Modified Nucleosides of tRNAs. II. Synthesis of 2'–O–methylcytidylyl (3'–5') cytidine,* Nucleic Acids Research, 2(6):951–960 (1975) Month of publication is unavailable.
Chavis et al., Synthesis of 2', 3'–Differentiated Ribonucleosides via Glycosylation Reactions with 2'–O'Me pr 2–O–TBDMS Ribofuranose Derivatives. 1. Pyrimidine Series, *J. Org. Chem.* 47:202–206 (1982, Jan. 15).
Heikkila et al., "5'–O–Trityl Group Promoted Directive Effect in the Preparation of 2'–O–Methylribonucleosides," *Acta Chemica Scandinavica* B36(10):715–717 (1982).

Inoue et al., "Synthesis and properties of novel nucleic acid probes," *Nucleic Acids Research Symposium Series No.* 16:165–168 (Nov. 6–8, 1985).
Inoue et al., "Synthesis and hybridization studies on two complementary nona(2'–O–methyl) ribonucleotides," *Nucleic Acids Research* 15:6131–6148 (1987), (Aug. 11, 1987),No. 15.
Wagner et al., "A Simple Procedure for the Preparation of Protected 2'–O–Methyl or 2'–O–Ethyl Ribonucleoside–3'–O–Phosphoramidites," *Nucleic Acids Research* 19:5965–5971 (1991) Nov. 11, No. 21.
Welch et al., "Some Aspects of Reactivity and Protection of the Imide Functions of Uridine and Guanosine in Nucleic Acid Synthesis," *Biophosphates and Their Analogues—Synthesis, Structure, Metabolism and Activity,* K.S. Bruzik and W. J. Stec editors, pp. 108–125 (1986) Month of publication data is not available.
Beijer et al., "Synthesis and Applications of Oligoribonucleotides with Selected 2'–O–Methylation Using the 2'–O–[1–(2–Fluorophenyl)–4–methoxypiperidin–4–yl] Protecting Group," *Nucleic Acids Research,* 18(17), 5143–5151 (Sep. 11, 1990).
Sinha et al., "Labile Exocyclic Amine Protection of Nucleosides in DNA, RNA and Oligonucleotide Analog Synthesis Facilitating N–Deacylation, Minimizing Depurination and Chain Degradation," *Biochemie,* 75(1–2), 13–23 (1993).
Vinayak et al., "Chemical Synthesis of RNA Using Fast Oligonucleotide Deprotection Chemistry," *Nucleic Acids Research,* 20(6), 1265–1269 (Mar. 25, 1992).
Beigelman et al., "Alternative Approaches to the Synthesis of 2'–O–Me Nucleosides," *Proceedings of the Eleventh International Roundtable on Nucleosides, Nucleotides and Their Biological Applications,* Leuven, Belgium, Sep. 7–11, 1994, published by Marcel Dekker in Nucleosides & Nucleotides, 14$^+$(3–5), 421–425 (1995).
Sproat et al., "New Synthetic Routes to Protected Purine 2'–O–Methylriboside–3'–O–phosphoramidites Using a Novel Alkylation Procedure," *Nucleic Acids Research,* 18(1), 41–49 (Jan. 11, 1990).
Nyilas et al., "Synthesis of $O^{2'}$–Methyluridine, $O^{2'}$–Methylcytidine, $N^4,O^{2'}$–Dimethylcytidine and $N^4$, $N^4$, $O^{2'}$–Trimethylcytidine From A Common Intermediate," *Acta Chem. Scand.,* B40(10), 826–830 (Nov. 1986).
Jager et al., "Synthesis of Deoxynucleoside Methylphosphonates Via a Phosphoramidite Approach," *Tetrahedron Letters,* 25(14), 1437–1440 (1984).

*Primary Examiner*—Marian C. Knode
*Assistant Examiner*—L. Eric Crane
*Attorney, Agent, or Firm*—Knobbe, Martens, Olson and Bear, LLP.

[57] ABSTRACT

Methods of preparing $N^4$–alkanoyl, aroyl and aralkanoyl 2'-O-methylcytidine derivatives are provided. Also provided are cytidine derivatives and nucleoside monomers comprising these cytidine derivatives which are useful in the synthesis of Oligomers, including oligonucleotides and methylphosphonate Oligomers.

1 Claim, 4 Drawing Sheets

Transamination of N-4-Benzoyldeoxycytidine
by Ethylenediamine

2'-O-METHYL CYTIDINE MONOMER USEFUL IN OLIGONUCLEOTIDE SYNTHESIS

This is a division of application Ser. No. 07/893,374 filed Jun. 3, 1992 hereby incorporated by reference in its totality (including drawings) now U.S. Pat. No. 5,606,049.

FIELD OF THE INVENTION

The present invention relates to the preparation of novel $N^4$-protected 2'-O-methyl cytidine monomers useful in the synthesis of Oligomers including oligonucleotides and methylphosphonate oligonucleosides.

BACKGROUND OF THE INVENTION

The present invention is directed to a novel $N^4$-protected, 2'-O-methyl cytidine monomer and methods for its preparation.

Oligonucleotides which include 2'-O-alkyl nucleosidyl units have been proposed as useful antisense probes for studying RNA processing. (Iribarren, A. M. et al., Proc. Natl. Acad. Sci. (USA) 87:7747–7751 (1990).

The 2'-O-methyl oligonucleotides have also been reported to inhibit certain mRNA processing events in vitro. See, e.g., Cotten, M, et al., Nucl. Acids. Res. 19(10):2629–2635 (1991).

Synthesis of 2'-O-methyl oligonucleotides has been reported using certain protected nucleotide monomers.

Since certain of the nucleotide monomers have reactive groups, such as the $N^4$ amino in cytidine and the $N^6$ amino in adenosine, these groups must be protected during synthesis of the Oligomer using protecting groups which are removable under non-adverse conditions after synthesis of the Oligomer is complete. Cytidine monomers having $N^4$-benzoyl protecting groups are conventionally used in oligonucleotide synthesis. See, e.g., Inoue, H., et al., Nucl. Acids Res. 15(15):6131–6147 (1987).

$N^4$-benzoyl-protected 2'-O-methyl cytidine has been found to undergo unwanted side reactions, particularly a transamination reaction, when treated with certain deprotecting reagents, in particular ethylenediamine which is used as a deprotecting reagent in the synthesis of methylphosphonate Oligomers. This transamination reaction has been found to result in decreased yields of methylphosphonate Oligomers.

SUMMARY OF THE INVENTION

The present invention is directed to methods of synthesizing compounds of the formula:

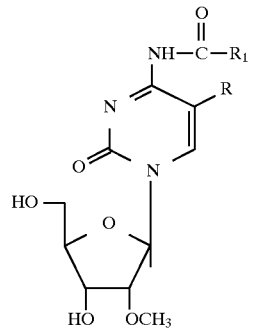

wherein R is hydrogen, fluorine or alkyl of 1 to 4 carbon atoms and $R_1$ is alkyl of about 1 to 6 carbon atoms, aryl of about 6 to 10 carbon atoms, or aralkyl of about 7 to about 12 carbon atoms. The compounds so prepared may then be converted into nucleoside monomers by processes such as those depicted in FIG. 2. and used in the synthesis of oligomers.

Acording to one aspect, the present invention is directed to a method of preparing a compound of formula (I). According to this aspect of the invention, cytidine or the corresponding 5-alkyl-cytidine is contacted with a dichlorotetraalkyldisiloxane under reacting conditions. The resulting mixture is then contacted with a 2'-O-trialkylsilylation reagent to give a 2'-O-trialkylsilyl intermediate. The 2'-O-trialkylsilyl intermediate is then contacted with a mixture of an acid chloride ($R_1C(O)Cl$) and a trialkylamine to give a $N^4$-alkanoyl, aroyl or aralkanoyl intermediate. The 2'-O-trialkylsilyl group is removed using a 2'-O-trialkylsilyl removing reagent to give an intermediate having a free 2'-hydroxy group, which is then contacted with a 2'-hydroxyl methylating reagent to give the corresponding $N^4$-alkanoyl or aroyl-2'-O-methyl-3', 5'-tetraalkyldisiloxane-cytidine derivative. That derivative is then contacted with a 3', 5'-tetraalkyldisiloxane removing agent to give the corresponding $N^4$-alkanoyl or aroyl-2'-O-methylcytidine of formula (I). Thus, according to one aspect of the present invention, the compounds of formula (I) above may be conveniently prepared by sequentially contacting a solution of cytidine or the corresponding 5-alkyl-cytidine under reacting conditions with (a) a dichlorotetraalkyldisiloxane, (b) a 2'-hydroxy trialkylsilation reagent, (c) a mixture of an acid chloride of the formula $R_1C(O)Cl$ and a trialkylamine; (d) a reagent which selectively removes the 2'-O-trialkylsilyl group under non-adverse conditions to give a free 2'-hydroxyl group; (e) a 2'-hydroxyl methylating reagent; and (f) a 3,5-tetraalkyldisiloxane removing reagent. Steps (a) to (d) may be conveniently conducted in situ, that is without isolation of any intermediate compounds.

FIG. 1(A) depicts a preferred aspect of the synthesis methods of the present invention. FIG. 1(B) depicts as a preferred embodiment of the present invention, namely the preparation of preferred compounds of formula (I) wherein $R_1$ is isopropyl.

According to one aspect, the present invention is directed to certain novel $N^4$-alkanoyl 2'-O-methyl cytidine derivatives, especially $N^4$-isobutyryl-2'-O-methyl cytidine (i.e., where R is hydrogen). These compounds are useful as intermediates in the preparation of nucleoside monomers used for oligonucleoside synthesis, particularly the synthesis of methylphosphonate oligomers.

These compounds, whose preparation according to a preferred embodiment of the present invention are depicted in FIG. 1(B), are particularly advantageous for use in the preparation of nucleoside monomers which may be used in the synthesis of methylphosphonate Oligomers. Suitable reaction schemes for the preparation of nucleoside monomers from one preferred compound, $N^4$-isobutyryl-2'-O-methylcytidine, are depicted in FIG. 2. When used in the synthesis of methyl phosphonate Oligomers, by methods such as those described in Example 7 herein, the resulting $N^4$-isobutyryl protected 2'-O-methylcytidine monomers offer certain advantages in comparison with the conventionally used $N^4$-benzoyl protected 2'-O-methyl cytidine monomers. When used in the synthesis of methyl phosphonate Oligomers, the $N^4$-benzoyl protected 2'-O-methyl cytidine monomers have been found to undergo an undesired side reaction during the step of deprotection and cleavage from the solid support, using the preferred reagent, ethylenediamine, used in synthesis of methylphosphonate Oligomers. This transamination side reaction is depicted in FIG. 3. This side reaction has been found to significantly reduce yields of methylphosphonate oligomers by up to about 15% per cytidine base. We have surprisingly found that the novel $N^4$-isobutyryl 2'-O-methyl cytidine monomers of the present invention do not undergo this transamination reaction and, therefore, their use will result in improved yields of methylphosphonate Oligomers.

Definitions

The term "alkyl" refers to saturated aliphatic groups including straight-chain, branched-chain and cyclic groups.

The term "aryl" refers to aromatic groups which have at least one ring having a conjugated pi electron system and includes carbocyclic aryl, heterocyclic aryl and biaryl groups, all of which may be optionally substituted.

The term "aralkyl" refers to an alkyl group substituted with an aryl group. Suitable aralkyl groups include benzyl, picolyl, and the like, and may be optionally substituted.

The term "alkanoyl" refers to the group —C(O)$R_1$ wherein $R_1$ is alkyl.

The term "aroyl" refers to the group —C(O)$R_1$ wherein $R_1$ is aryl.

The term "aralkanoyl" refers to the group —C(O)$R_1$ wherein $R_1$ is aralkyl.

The term "alkoxy" refers to the group —OR' wherein R' is alkyl.

The term "aryloxy" refers to the group —OR' wherein R' is aryl.

The term "nucleoside" includes a nucleosidyl unit and is used interchangeably therewith, and refers to a subunit of a nucleic acid which comprises a 5 carbon sugar and a nitrogen- containing base. The term includes not only units having A, G, C, T and U as their bases, but also analogs and modified forms of the bases (such as 8-substituted purines). In RNA, the 5 carbon sugar is ribose; in DNA, it is a 2'-deoxyribose. The term also includes analogs of such subunits, including modified sugars such as 2'-O-alkyl ribose.

The term "phosphonate" refers to the group

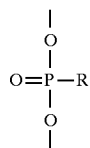

wherein R is an alkyl or aryl group. Suitable alkyl or aryl groups include those which do not sterically hinder the phosphonate linkage or interact with each other. The phosphonate group may exist in either an "R" or an "S" configuration. Phosphonate groups may be used as internucleosidyl phosphorus group linkages (or links) to connect nucleosidyl units.

The term "phosphodiester" refers to the group

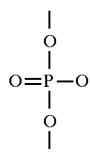

wherein phosphodiester groups may be used as internucleosidyl phosphorus group linkages (or links) to connect nucleosidyl units.

The term "oligonucleoside" or "Oligomer" refers to a chain of nucleosides which are linked by internucleoside linkages which is generally from about 6 to about 100 nucleosides in length, but which may be greater than about 100 nucleosides in length. They are usually synthesized from nucleoside monomers, but may also be obtained by enzymatic means. Thus, the term "Oligomer" refers to a chain of oligonucleosides which have internucleosidyl linkages linking the nucleoside monomers and, thus, includes oligonucleotides, nonionic oligonucleoside alkyl- and aryl-phosphonate analogs, alkyl- and aryl-phosphonothioates, phosphorothioate or phosphorodithioate analogs of oligonucleotides, phosphoramidate analogs of oligonucleotides, neutral phosphate ester oligonucleoside analogs, such as phosphotriesters and other oligonucleoside analogs and modified oligonucleosides, and also includes nucleoside/non-nucleoside polymers. The term also includes nucleoside/nucleotide polymers wherein one or more of the phosphorus group linkages between monomeric units has been replaced by a non-phosphorous linkage such as a formacetal linkage, a sulfamate linkage, or a carbamate linkage. It also includes nucleoside/non-nucleoside polymers wherein both the sugar and the phosphorous moiety have been replaced or modified such as morpholino base analogs, or polyamide base analogs. It also includes nucleoside/non-nucleoside polymers wherein the base, the sugar, and the phosphate backbone of the non-nucleoside are either replaced by a non-nucleoside moiety or wherein a non-nucleoside moiety is inserted into the nucleoside/non-nucleoside polymer. Optionally, said non-nucleoside moiety may serve to link other small molecules which may interact with target sequences or alter uptake into target cells.

The term "alkyl- or aryl-phosphonate Oligomer" refers to Oligomers having at least one alkyl- or aryl-phosphonate internucleosidyl linkage. Suitable alkyl- or aryl-phosphonate groups include alkyl- or aryl- groups which do not sterically hinder the phosphonate linkage or interact with each other. Preferred alkyl groups include lower alkyl groups having from about 1 to about 6 carbon atoms. Suitable aryl groups have at least one ring having a conjugated pi electron system and include carbocyclic aryl and heterocyclic aryl groups, which may be optionally substituted and preferably having up to about 10 carbon atoms.

The term "methylphosphonate Oligomer" (or "MP-Oligomer") refers to Oligomers having at least one methylphosphonate internucleosidyl linkage.

The term "non-adverse conditions" describes conditions (of reaction or synthesis) which do not substantially adversely affect the Oligomer skeleton and its sugar, and base components, nor the solid support. One skilled in the art can readily identify functionalities, coupling methods, deblocking and deprotection procedures and cleavage conditions which meet these criteria.

The term "nucleoside monomer," "monomeric unit" or "monomer" refers to a reagent which adds a nucleosidyl unit to a growing Oligomer chain by a coupling reaction such as that used in oligonucleotide synthesis (See, e.g., U.S. Pat. No. 4,725,677, to Koster, et al. the disclosure of which is incorporated herein by reference) or synthesis of methylphosphonate Oligomers (see Example 7 herein). Typical nucleoside monomers comprise a nucleosidyl unit having a blocking group attached to the 5'-oxygen and a trivalent phosphorus group attached to the 3'-oxygen, wherein the phosphorus group can form an internucleoside linkage with a hydroxyl group under coupling conditions. Such suitable nucleoside monomers include 3'-diisopropyl-methylphosphonamidite-5'-dimethoxytrityl, 3'-β-cyanoethyl-diisopropylphosphoramidite-5'-dimethoxytrityl and 3'-diisopropylmethoxyphosphoramidite-5'-dimethoxytrityl derivatives of nucleosides.

DETAILED DESCRIPTION OF THE INVENTION

1. Preferred Compounds
   a. Preferred Cytidine Derivatives

According to one aspect, the present invention provides certain novel cytidine derivatives of the formula

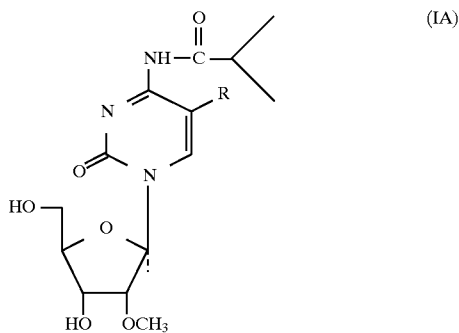

(IA)

wherein R is hydrogen, fluorine or alkyl. These cytidine derivatives may be used to prepare nucleoside monomers which may be then used in the synthesis of Oligomers, including oligonucleotides and methylphosphonate Oligomers.

b. Preferred Nucleoside Monomers

According to an alternate aspect, the present invention is directed to certain novel nucleoside monomers of the formula

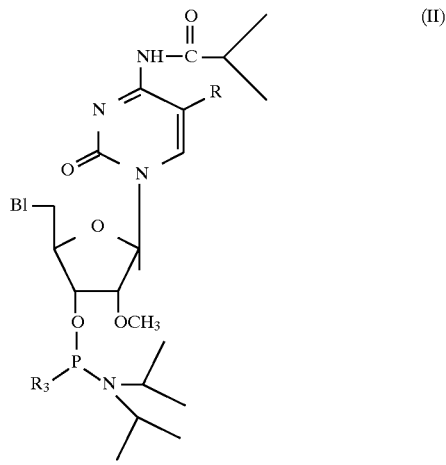

(II)

wherein R is as defined in conjunction with formulas I and Ia hereinabove, $R_3$ is alkyl, aryl, optionally substituted alkoxy or optionally substituted aryloxy; and Bl is a removable blocking group. Preferred blocking groups, Bl, include the acid labile 4,4'-dimethoxytrityl ("DMT") or 4,4',4"-trimethoxytrityl groups, as well as other such blocking groups conventionally used in the synthesis of oligomers.

These nucleoside monomers are useful in the synthesis of Oligomers. Thus, according to a further aspect, the present invention is directed to methods of preparing oligomers, such as oligonucleosides and methylphosphonate oligomers using the nucleoside monomers of formula (II). oligonucleotides may be prepared using procedures such as those disclosed in U.S. Pat. No. 4,725,677, the disclosure of which is incorporated herein by reference and methylphosphonate oligomers using methods such as described in Example 7 herein.

These Oligomers which are made using these nucleoside monomers may be used in a variety of applications, including as antisense Oligomers to prevent or decrease expression of a target nucleic acid sequence, and to prevent or decrease expression of a product of a selected gene.

2. Preparation of Preferred Compounds and Preferred Reaction Conditions

FIG. 1(A) depicts a reaction scheme for a preferred aspect of the methods of the present invention and FIG. 1(B) depicts the preparation of the preferred compound of formula (I), including the especially preferred compound, $N^4$-isobutyryl-2'-O-methylcytidine (R=hydrogen), according to the methods of the present invention.

a. Preparation of $N^4$-Isobutyryl-3', 5'-Tetraisopropyldisiloxane-1,3-diyl-cytidine (1)

Figure 1:
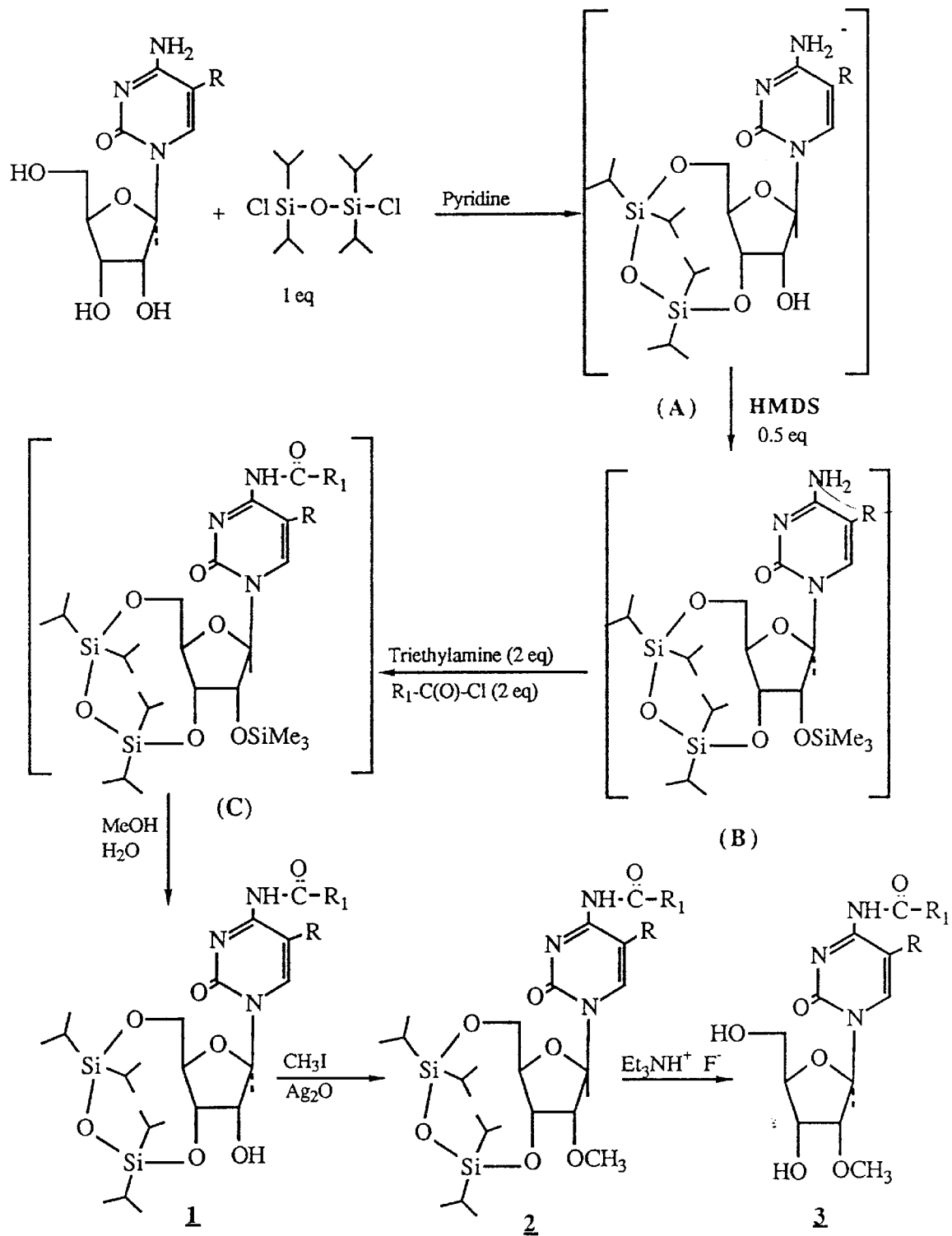
FIG. 1(A) depicts a synthseis scheme for the preparation of compounds of formula (I) according to a preferred aspect of the present invention.
FIG. 1(B) depicts the synthesis scheme for the preparation of $N^4$-isobutyryl-2'-O-methyl cytidine according to the process of the present invention.
Figure 1:
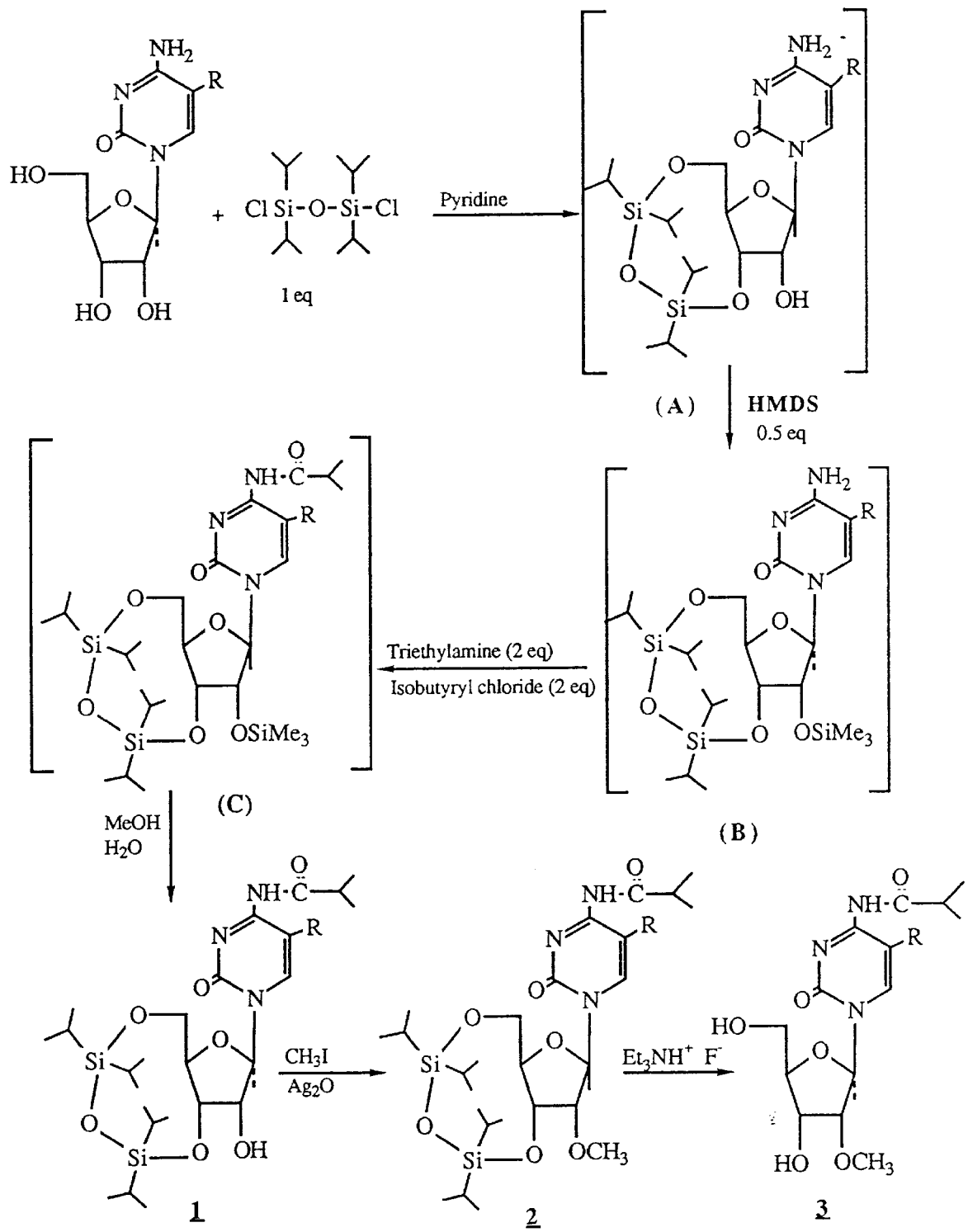
Figure 2:
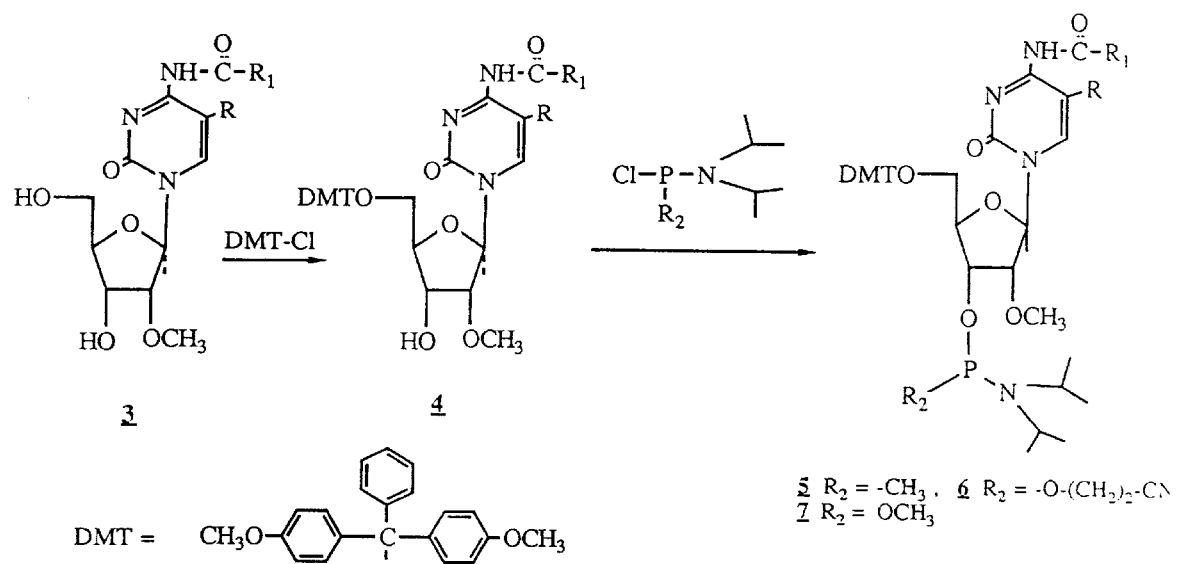
FIG. 2 depicts the synthesis of nucleoside monomers from $N^4$-isobutyryl-2'-O-methylcytidine.
Figure 3:
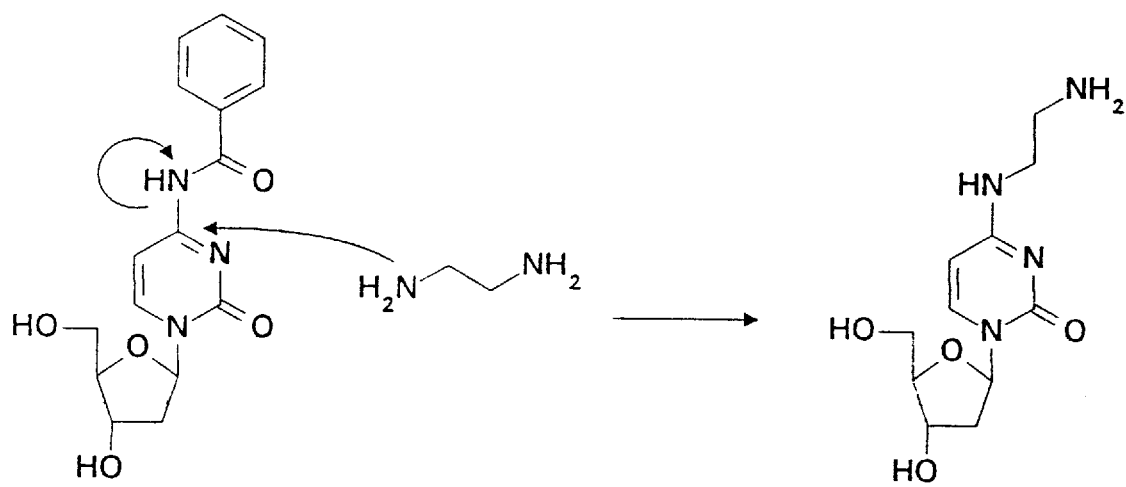
FIG. 3 depicts the transamination reaction of N-benzoyldeoxycytidine by ethylenediamine.

According to the process of the invention, $N^4$-isobutyryl-3', 5'-tetraisopropyldisiloxane-1,3-diyl-cytidine (1) is conveniently prepared directly from cytidine without requiring isolation of the proposed intermediates (A), (B) and (C) which are depicted in brackets in FIG. 1. Other suitable 3', 5'-protecting groups which may be used in place of the tetraisopropyldisiloxane group include the tetra-t-butoxydisiloxane group and other tetraalkyldisiloxanes. These 3', 5'-tetraalkyldisiloxanes may be prepared by procedures analogous to those described below.

Preferably cytidine is dried to remove small amounts of water which may be present prior to the first reaction step. According to this reaction step, dichlorotetraisopropyldisiloxane is added to cytidine in a suitable solvent. Suitable solvents include polar anhydrous organic solvents such as pyridine, dimethylformamide (DMF) supplemented with base. At least 1 equivalent dichlorotetraisopropyldisiloxane (DCTPS) per equivalent cytidine is used, preferably, from about 1.0 to about 2.4 equivalents DCTPS per equivalent cytidine, more preferably from about 1.0 to about 1.2 equivalents of DCTPS per equivalent cytidine, or alternatively, approximately equivalent amounts of DCTPS and cytidine are used. The reaction is conducted at a temperature of about 15° C. to about 40° C., preferably from about 22° C. to about 25° C. or, for convenience at ambient temperature and pressure. The reaction is generally complete within about 1 to about 4 hours. Completion of this reaction may be conveniently monitored by using methods such as thin later chromatography (TLC). The product, proposed intermediate (A), is conveniently used in the next reaction step without further isolation.

Quantitative trimethylsilylation is then performed by adding a trimethylsilation reagent, such as hexamethyldisilazane (HMDS), to the reaction mixture. Preferably, HMDS is added in the amount of about 0.5 to about 1.0 equivalents HMDS per equivalent cytidine, more preferably about 0.5 to about 0.6 equivalents HMDS per equivalent cytidine are used. The reaction is conducted at a temperature of about 15° C. to about 40° C., preferably from about 22° C. to about 25° C. or for convenience at ambient temperature and pressure. The reaction is generally complete within about 15 minutes to about 2 hours. Completion of the trimethylsilylation reaction is conveniently monitored using TLC. Other suitable 2'-protecting groups include other trialkylsilyl groups. Other suitable trialkylsilylation reagents include chlorotrimethylsilane. The product, proposed intermediate (B), is conveniently used in the subsequent reaction step without further isolation.

To the mixture containing the intermediate from the previous step, triethylamine (about 1.2 to about 3.0 equivalents, preferably from about 1.2 to about 2.2 equivalents per equivalent cytidine) and isobutyryl chloride (about 1.2 to about 3 equivalents, preferably from about 1.8 to about 2.2 equivalents isobutyryl chloride per equivalent cytidine) are added, preferably with stirring. Preferably approximately equimoler amounts of isobutyryl chloride and trialkylamine are employed. Other trialkyl amines may be used in place of triethylamine. The reaction is conducted at a temperature of from about 15° C. to about 30° C., preferably from about 15° C. to about 24° C., or for convenience at ambient temperature and pressure. The reaction is generally complete in about 30 minutes to about 4 hours. Completion of the reaction may be conveniently monitored using TLC.

The 2'-O-silyl group may be conveniently removed by hydrolysis, such as by the addition of an aliquot of methanol/water or alternatively water alone at ambient temperature and is generally complete in about an hour.

The product, $N^4$-isobutyryl -3', 5'-tetraisopropyldisiloxane-1,3-diyl-cytidine (1) may be isolated by conventional techniques such as evaporation, extraction, chromatography and the like.

b. Preparation of $N^4$-Isobutyryl-2'-O-methyl-3', 5'-tetraisopropyldisiloxane-1,3-diyl-cytidine (2)

The 2'-hydroxyl of the $N^4$-isobutyryl-3', 5'-tetraisopropyldisiloxane-1,3-diyl-cytidine may be conveniently methylated to give the 2'-O-methyl derivative by reacting it with methyl iodide (about 10 to about 40 equivalents, preferably from about 18 to about 22 equivalents of methyl iodide per equivalent cytidine) and silver oxide (about 2.5 to about 4 equivalents, preferably from about 2.8 to about 3.2 equivalents silver oxide per equivalent cytidine) in solvent. The reaction is conducted at a temperature of about 15° C. to about 40° C., preferably from about 22° C. to about 25° C., or , for convenience at ambient temperature and pressure. Completion of the reaction may be conveniently monitored using TLC. The product, $N^4$-isobutyryl-2'-O- methyl-3', 5'-tetraisopropyldisiloxane-1,3-diyl-cytidine (2) is isolated using conventional procedures such as evaporation, filtration, extraction, chromatography and the like.

c. Preparation of $N^4$-Isobutyryl-2'-O-methyl-cytidine (3)

The 3', 5'-tetraisopropyldisiloxane group is removed from $N^4$-isobutyryl-2'-O-methyl-3', 5'-tetraisopropyl-disiloxane-1,3-diyl-cytidine by treatment with freshly prepared triethylammonium hydrofluoride. The reaction is preferably conducted by adding the tetraisopropylsiloxane-protected cytidine to the freshly prepared triethylammonium hydrofluoride mixture. The triethylammonium hydrofluoride mixture may be conveniently prepared by dissolving triethylamine and hydrogen fluoride solution (aqueous) in an aprotic solvent such as methanol, ethanol or the like and then removing the solvent by evaporation, and followed by the addition of more solvent (such as dioxane, tetrahydrofuran (THF) and the like) and evaporation of solvent to a residue and repeating the addition/evaporation procedure. The residue is then dissolved in solvent, preferably a mixture of dioxane and tetrahydrofuran, and the pH is adjusted to give a neutral to slightly basic (about 7 to 7.5) pH. Other tetraalkylammonium fluoride or trialkylammonium hydrofluoride solutions which are prepared using similar methods to those described above may be used. The fluoride solution so obtained is then added to the tetraisopropyldisiloxane-cytidine. The reaction is conducted at a temperature of about 15° C. to about 40° C., preferably from about 22° C. to about 25° C., or for convenience at ambient temperature and pressure. The reaction is generally complete within about 8 to about 24 hours. For convenience, the reaction may be conducted by stirring at room temperature overnight. Completion of the reaction may be conveniently monitored using TLC. The product may be isolated using conventional procedures such as extraction, precipitation, evaporation filtration, chromatography and the like. The product may be conveniently purified by isolation using a flash silica gel column.

d. Preparation of $N^4$-isobutyryl-2'-O-methyl cytidine phosphonamidites or phosphoramidites The $N^4$-isobutylryl-2'-O-methyl cytidines of the present invention may be conveniently converted to the corresponding diisopropylmethylphosphonamidite or β-cyanoethyl phosphoramidite derivatives useful in automated synthesis of oligonucleotides and methylphosphonate Oligomers by conventional methods such as those described in Examples 4 to 6 herein including protection of the 5'-hydroxyl group with a dimethoxytrityl group and conversion of the 3'-hydroxyl group to a diisopropylmethylphosphon-amidite (5) or β-cyanoethyl-diisopropylphosphonamidite (6) group.

To assist in understanding the present invention, the following examples are included which describe the results of a series of experiments. The following examples relating to this invention should not, of course, be construed in specifically limiting the invention and such variations of the invention, now known or later developed, which would within the purview of one skilled in the art are considered to fall within the scope of the present invention as hereinafter claimed.

EXAMPLES

Example 1

Preparation of $N^4$-isobutyryl-3', 5'-tetraisopropyldisiloxane-1,3-diyl-cytidine (1)

In a 1 liter round bottom flask, 30 g (123 mmole) of cytidine was dried by co-evaporation with pyridine and dissolved in 350 ml of anhydrous pyridine. To this solution 39 g (123 mmole, 1 eq.) of dichlorotetraisopropyl-disiloxane (DCTPS) was added slowly and the reaction mixture was stirred at room temperature until the completion of the reaction (about 2 hours) which was observed by TLC. To this mixture, 9.96 g hexamethyldisilazane (HMDS) (62 mmole, 0.5 eq.) was added and stirred for 1 hour. Completion of the quantitative trimethylsilylation reaction of 2'-hydroxyl was monitored by TLC. To this resulting mixture, 2 equivalents of triethylamine (246 mmoles) and 2 equivalents of isobutyryl chloride (26.2 g, 246 mmoles) were added and stirring was continued at room temperature for another 2 hours. Quantitative blocking of the exocyclic amine was observed by TLC. The 2'-silyl group was then removed by addition of 60 ml of methanol/water (1:1) over one hour. The solvents were removed using a rotary evaporator and the residue obtained was dissolved in 300 ml of dichloromethane. The mixture was extracted with 2×50 ml of saturated sodium bicarbonate solution and washed with 50 ml of water. The organic solution was dried ($MgSO_4$) and evaporated to give 63 g of a product which was >95% pure (89% yield). A 2 g sample of this material was purified on a flash silica gel column for analytical purposes. The bulk of the product was used in the next reaction without further purification.

$^1$H NMR in CDCl$_3$, δ ppm: 1.24 (dd, 6H, CH$_3$ of isobutyryl), 2.63 (m, 1H, C$\underline{H}$(CH$_3$)), 5.84 (5, 1H, H'$_1$, anomeric proton), 7.43 (d, 1H, H$_6$), 8.19 (d, 1H, H$_5$), also other sugar and isopropyl protons.

Example 2

Preparation of N$^4$-isobutyryl-2'-O-methyl-3', 5'-tetraisopropyldisiloxane-1,3-diyl-cytidine (2)

In a 1 liter round bottom flask, 55 g of the product of Example 1 (0.1 mole) was dissolved in 350 ml of benzene. To this solution, 284 g of methyl iodide (20 eq., 2 moles) and 69.5 g silver oxide (3 eq., 0.3 mole) were added and the resulting mixture stirred at room temperature for 2 hours. The progress of the reaction was monitored by TLC. Quantitative methylation was observed in 2 hours. The solvent was removed by evaporation and the residue was taken up in 200 ml of methylene chloride and filtered through a layer of celite. The clear solution was extracted with 2×50 ml of water. The organic phase was separated and dried (MgSO$_4$) and loaded on a layer of 230–400 mesh silica gel and washed with 2% methanol in dichloromethane. A trace of silver oxide was identified in this product which was removed by extraction with 0.5M ammonium chloride solution (2×50 ml extractions). The solution was then evaporated to dryness which gave 56.9 g of the above-identified product (98% pure TLC). Yield was 97%. This product was used in the synthesis described by in Example 3 without further purification. A 2 g sample was further purified on a silica gel column for analytical evaluation.

$^1$H NMR in CDCl$_3$, δ ppm: 2'-O-methyl at 1.74 ppm; other protons were similar to those observed with the product of Example 1.

Example 3

Preparation of N$^4$-isobutyryl-2'-O-methyl-cytidine (3)

Triethylammonium hydrofluoride was prepared freshly by dissolving 73 ml of triethylamine and 27 g of 50% HF solution in 500 ml methanol. The solvent was removed by rotavap to reduce the volume to 30 ml. The residue was taken up in 100 ml dioxane and evaporated to dryness. The dioxane co-evaporation was repeated twice. The residue was dissolved in 250 ml dioxane and 250 ml tetrahydrofuran (~1M). The pH was adjusted to about 7 to 7.5 by adding triethylamine (~30 ml). To 52 g of the product of Example 2, 200 ml of the fluoride solution was added and the resulting mixture was stirred at room temperature overnight. TLC showed a major product and two minor spots which ran faster on silica gel. The reaction mixture was shaken with 200 ml of saturated NaHCO$_3$ and 500 ml of methylene chloride which resulted in formation of a precipitate. The precipitate and the CH$_2$Cl$_2$ phase were separated, mixed and dried. The residue was dissolved in 300 ml hot methanol and filtered. After evaporation of methanol, 32 g of solid was obtained which contained the desired product and which was purified on a flash silica gel column to yield 22.4 g of the above-identified product (75% yield).

Hydrolysis of the isobutyryl group with ammonium hydroxide gave 2'-O-methylcytidine which showed a UV spectrum and HPLC analysis identical to the reference purchased from Sigma.

Example 4

Preparation of 5'-dimethoxytrityl-N$^4$-isobutyryl-2'-O-methyl-cytidine (4)

Compound 3 (14.5 g, 44 mmole), the product of Example 3, was dried by co-evaporation with dry pyridine and dissolved in 100 ml of dry pyridine. A solution of 16 g of dimethoxytriyl chloride (47 mmole, 1.07 equiv.) in 100 ml of CH$_2$Cl$_2$/pyridine (1:1) was added dropwise with stirring. The reaction continued at room temperature for 45 minutes. The progress of the reaction was monitored by TLC. After the completion of the reaction, it was quenched by the addition of 20 ml methanol, followed by stirring of the resulting mixture for 10 minutes. The solvents were removed under reduced pressure. The residue was dissolved in 50 ml of dichloromethane and extracted with saturated sodium hydrogen carbonate (2×50 ml) followed by water (30 ml). The organic phase was dried (MgSO$_4$) and filtered. After the evaporation of the solvent, the residue was purified with a flash column chromatography. The product was eluted with 2% methanol in dichloromethane containing 0.5% triethylamine. Yield was 22.38 of the above-identified compound (about 80%).

Example 5

Preparation of 3'-diisopropylmethylphosphonamidite-5'-dimethoxytrityl-N$^4$-isobutyryl-2'-O-methyl-cytidine (5)

The DMT blocked nucleoside, compound 4 (16 g, 25.4 mmol) (the product of Example 4), was dried by co-evaporation with dry pyridine and the residue was dissolved in 80 ml of anhydrous dichloromethane. Under a closed argon atmosphere, 1.5 equivalents of diisopropylethylamine (15 g, 38 mmole) were added and the mixture was cooled to 0° C. in an ice bath and 1.2 equivalents of N,N-diisopropylmethyphosphinamidic chloride [(CH$_3$)$_2$CH]$_2$NP(CH$_3$)Cl (30 mmole) were added dropwise. The reaction was complete in 45 minutes. The solvent was removed under reduced pressure and the residue was purified on a flash Silica Gel column. The column was packed with ethyl acetate/hexane (1:1) containing 5% triethylamine and washed with the ethyl acetate/hexane containing 1% triethylamine. The reaction mixture was then loaded on the column and the product was eluted with ethyl acetate/hexane (1:1) containing 1% triethylamine. The product was dried to give 14.0 g of the above-identified product as a foamy material (yield 71%).

Example 6

Preparation of 3'-6-cyanoethyl-diisopropylphosphonamidite-5 '-dimethoxytrityl-N$^4$-isobutyryl-2 '-O-methyl-cytidine (6)

Compound 6 was prepared by coupling of the compound 4 (the product of Example 4) with 2-cyanoethyl N,N-diisopropylchlorophosphoramidite [CH$_3$)$_2$CH]$_2$NP(Cl)OCH$_2$CH$_2$CN by procedures similar to the preparation of Compound 5 described in Example 5.

Example 7

Synthesis of oligonucleoside methylphosphonates and 2'-O-methyl oligonucleoside methylphosphonates Oligomers were synthesized using 2'-O-methyl-cytidine monomer (Compound 5, the product of Example 5) and 5'-(dimethoxytrityl)-nucleoside-3'-[(N,N-diisopropylamino) methyl]phosphonamidite monomers of dA, T and dG. Solid-phase synthesis was performed on methacrylate polymer supports with a Biosearch Model 8750 DNA synthesizer according to the manufacturer's recommendations except for the following modifications: monomers were dissolved in either 1:1 acetonitrile/dichloromethane ("dG") or acetonitrile ("dA", "dC" and "T") at concentrations of 100 mM. DEBLOCK reagent=2.5% dichloroacetic acid in dichloromethane. OXIDIZER reagent=25 g/L iodine in 0.25% water, 25% 2,6-lutidine, 72.5% tetrahydrofuran. CAP A=10% acetic anhydride in acetonitrile. CAP B=0.625% N,N-dimethylaminopyridine in pyridine.

The dimethoxytriyl group was removed from the oligonucleotide at the end of the synthesis.

The oligonucleotide was then cleaved from the support and deprotected. The support bound oligonucleotide was removed from the synthesis cartridge and placed in a glass 1 dram vial with a screw top. The support was treated for 30 minutes at room temperature with 1 ml of a solution of acetonitrile/ethanol/water (9/9/1) saturated with ammonia gas (approximately 9% w/w). Then, 1 ml of ethylenediamine was added to the reaction vessel and the reaction allowed 6 hours to go to completion. The supernatant containing the oligonucleotide was then removed from the support and the support rinsed twice with 2 ml of 1/1 acetonitrile/water, when was combined with the supernatant. The combined solution was diluted to 30 ml total volume with water and neutralized with approximately 4 ml of 6 N HCl. The neutralized solution was desalted using a Waters C-18 Sep-Pak cartridge which was pre-equilibrated with 10 ml acetonitrile, 10 ml 50% acetonitrile/100 mM triethylammonium bicarbonate, and 10 ml 25 mM triethylammonium bicarbonate, sequentially. After the reaction solution was passed through the column it was washed with 30 ml of water. The product was then eluted with 5 ml of 1/1 acetonitrile/water.

The oligonucleotide was purified by HPLC on a reverse phase column (Whatman RAC II) using a gradient of acetonitrile in 50 mM triethylammonium acetate.

I claim:

1. 3'-diisopropylmethylphosphonamidityl-5'-dimethoxytrityl-$N^4$-isobutyryl-2'-O-methylcytidine.

* * * * *